United States Patent [19]

Kuehn et al.

[11] Patent Number: 5,063,151
[45] Date of Patent: Nov. 5, 1991

[54] IMMUNOASSAY METHOD AND KIT
[75] Inventors: Christa G. Kuehn, Princeton Junction, N.J.; Debra J. Rossi, Yardley, Pa.; Stephan S. Isied, Princeton, N.J.
[73] Assignee: Biometallics, Inc., Princeton, N.J.
[21] Appl. No.: 778,554
[22] Filed: Sep. 20, 1985
[51] Int. Cl.⁵ .................. G01N 33/535; G01N 33/554
[52] U.S. Cl. .................................. 435/7.33; 435/7.9; 435/7.91; 435/7.92; 435/963; 435/966; 435/975; 436/519; 436/534; 436/535; 436/547; 436/817; 436/828; 530/402; 530/817; 427/2
[58] Field of Search .................. 424/7.1; 435/7, 180, 435/810, 7.33; 436/65, 610, 519, 531, 535, 547, 814, 817, 828, 533, 534; 530/387, 402, 817

[56] References Cited

U.S. PATENT DOCUMENTS

| | | | |
|---|---|---|---|
| 3,654,090 | 4/1972 | Schuurs et al. | 435/7 |
| 3,770,383 | 11/1973 | Price | 436/531 X |
| 3,888,629 | 6/1975 | Bagshawe | 23/230 |
| 3,995,018 | 11/1976 | Sjöquist | 436/531 X |
| 4,230,664 | 10/1980 | Cais | 422/61 |
| 4,235,601 | 11/1980 | Deutsch et al. | 23/230 |
| 4,279,885 | 7/1981 | Reese et al. | 436/519 X |
| 4,280,816 | 7/1981 | Elahi | 435/7 |
| 4,292,296 | 9/1981 | Parsons, Jr. | 436/518 X |
| 4,376,110 | 3/1983 | David et al. | 436/513 |
| 4,394,444 | 7/1983 | Cameron et al. | 435/28 X |
| 4,399,229 | 8/1983 | Kelton et al. | 436/519 |
| 4,517,288 | 5/1985 | Giegel et al. | 435/7 |
| 4,592,996 | 6/1986 | Yamanishi et al. | 435/28 X |

FOREIGN PATENT DOCUMENTS

| | | | |
|---|---|---|---|
| 0659059 | 3/1963 | Canada | 435/180 |
| 0125118 | 5/1983 | European Pat. Off. | 435/7 |
| 8505451 | 12/1985 | PCT Int'l Appl. | 435/7 |
| 1125549 | 11/1982 | U.S.S.R. | 436/519 |

OTHER PUBLICATIONS

Jungers et al., J. Lab. Clin. Medicine 98, 30–36 (1981).
"The Use of Protein A-Containing *Staphylococcus Aureus* as a Solid Phase Anti-IgG Reagent in Radioimmunoassays as Exemplified in the Quantitation of α-Fetoprotein in Normal Human Adult Serum", Johnson, S. and Kronvall, G., Eur. J. Immunmol. 4:29–33, 1974.
"Detection of Membrane-Associated Antigens on Lymphoid Cells by Antibody Coupled to Staphylococcal Protein A", Kearney et al., The Journal of Immunology, vol. 114, No. 4, Apr., 1975.
"Rapid Isolation of Antigens from Cells with a Staphylococcal Protein A-Antibody Adsorbent: Parameters of the Interaction of Antibody-Antigen Complexes with Protein A", Kessler, S. W., The Journal of Immunology, vol. 115, No. 6, Dec., 1975.
"Cell Membrane Antigen Isolation with the Staphylococcal Protein A-Antibody Adsorbent", Kessler, S. W., The Journal of Immunology, vol. 117, No. 5, Part 1, Nov., 1976.
"Use of Immunoglobulin-Loaded Protein A-Bearing Staphylococci as a Primary Solid Phase Immunoadsorbent in Radioimmunoassay", O'Keefe, E. O. and Bennett, V., The Journal of Biological Chemistry, vol. 255, No. 2, Jan., 1980.
"Dipstick Method for Human Chorionic Gonadotropin Suitable for Emergency Use on Whole Blood and Other Fluids", Norman, R. J., et al., The Lancet, Jan. 5, 1985.
"ImmunoConcentration ™—A New Format for Solid-Phase Immunoassays", Valkirs, G. E., and Barton, R., Clinical Chemistry, vol. 31, No. 9, 1985.
"You're Looking at a Revolutionary Application of Monoclonal Antibody Technology: ImmunoConcentration ™", anonymous undated brochure published by Hybritech, Inc., San Diego, California.

*Primary Examiner*—Esther L. Kepplinger
*Attorney, Agent, or Firm*—Walter A. Hackler

[57] ABSTRACT

A method of binding an antibody with protein A cells is provided which includes a sequence of incubation and dilution steps to produce a preselected amount and concentration of antibody with a preselected distribution of antibody among the protein A cells. In addition, a method is provided for preparing an antibody entrapped porous matrix and apparatus which includes a specific porous matrix with a preselected position of antibody bound bacterium cells therein along with means for drawing fluids through the porous medium and means for facilitating the deposition of fluids onto the surface of the porous matrix. The apparatus and method is useful for testing for the level of progesterone in animal body fluids, such as milk, plasma, serum, whole blood and saliva.

40 Claims, 4 Drawing Sheets

FIG. 1

FIG. 2
(KNOWN ART)

PROGESTERONE ng/ml

BACKGROUND ABSORBANCE

IMMUNOASSAY METHOD AND KIT

The present invention is generally directed to immunoassay methods and more particularly directed to an immunoassay method and kit in which three dimensional antibody protein A cell wall complexes are physically entrapped in a porous matrix.

The present invention is of particular importance in determining the concentration of the steroid hormone, progesterone in animal body fluid for determination of the correct time for insemination and/or for early detection of pregnancy. The method and kit of the present invention has a special advantage in that such determination of progesterone can be done in the field without equipment other than the kit itself which is disposable after use.

Immunoassay techniques have been known for many years and include radioimmunoassay, enzyme immunoassay and fluorescent immunoassay.

In all of these techniques a labelled antigen attaches itself to a preselected antibody during the assay and the amount of labelled antigen combining with the antibodies is thereafter determined.

In the case of radioimmunoassay, the antigen is labelled with a radioactive element, whereas in enzyme or fluorescent immunoassay the labelling is done with an enzyme or a component capable of fluorescing. It should be readily apparent that radioactive labelled antigens are detected with radioactivity detectors and fluorescent labelled antigens with fluorescence detectors.

It is readily apparent to one skilled in the art that both the radioimmunoassay techniques and the fluorescent immunoassay techniques require specialized equipment, such as radiation counters or special lighting, in order to conduct the assay. These tests are therefore well suited for laboratories in which proper use and safety precautions with regard to this equipment may be controlled.

However, the radioimmunoassay and fluorescent immunoassay techniques are not suitable for in-field determination of antigen levels in animal fluids.

On the other hand, enzyme labelled antigens may be detected by adding a substrate (reactant) thereto to produce a colored reaction product which can be visually observed.

Because no specialized laboratory equipment need be used, enzyme immunoassay techniques have greater possibility for use in in-field immunoassay than radioimmunoassay or fluorescent immunoassay techniques. This is of particular importance to breeders of cattle, horses and pigs, for example.

It is well known that progesterone arises from the corpus luteum gland in the ovary during the luteal phase of the menstrual cycle and from the placenta during pregnancy.

The lowest progesterone level in animals corresponds to estrus (time of ovulation) and the highest progesterone level occurs near the midpoint of a normal ovarian cycle.

During the cycle, the progesterone level will drop to, or below, 5 ng/ml during estrus and thereafter rise to a level of between 10–30 ng/ml, depending upon the animal.

Usually, following the drop of the progesterone level to about 5 ng/ml, insemination is effected to impregnate the animal. Thereafter, high progesterone levels during days 18-22 of the cycle indicate pregnancy.

Since in all modern cattle breeding operations, artificial insemination is utilized, an important use of immunoassay techniques is the determination of progesterone levels.

At the present time, estrus is detected visually, but frequently, animals show no visible signs corresponding to estrus and as a result, estrus is incorrectly detected.

It is obvious when this occurs that a delay of about 21 days will occur before artificial insemination can result in pregnancy.

This represents a significance loss of time and money for the breeder, hence, an accurate in-field progesterone level assay method and kit is very desirable.

As hereinbefore pointed out, radioimmunoassay and fluorescent immunoassay are not suitable for in-field use and hence cannot satisfy the needs of cattle breeders.

Time is also an important aspect in the development of an acceptable in-field immunoassay technique for progesterone levels. Since the test must be individually performed for each of thousands of animals in a large scale breeding operation, tests which require hours, or days, are impractical.

This problem was addressed in U.S. Pat. No. 4,399,229 to Kelton, et al. In an attempt to create a radioimmunoassay method requiring less time, Kelton bound antibodies to protein A, the protein A being associated with the cell wall of the bacterium *Staphylococcus aureus*.

This method reduces the incubation time necessary when a free antibody is used, as is well known in the art.

The advantage in utilizing protein A cells arises from the fact that protein A binds to the $F_c$ portion of almost all antibodies and, since it has four $F_c$ binding regions per protein A molecule, the protein A both orients the antibody molecules and concentrates the number of antibody molecules in a given volume.

The result is a three-dimension, structurally well organized network with antibody molecules oriented on the surface of the protein A molecules and extending from the cell walls.

It is important that unpurified protein A, which includes the cell walls, is utilized in order that the cell walls provide both physical size and organiation to the antibody complex.

The resultant large size enables the protein A-antibody-complex to be suspended in a filter matrix, or the like.

In spite of an increasing amount of research and development in this area and the significant strides that have been accomplished, no practical, fast, efficient and cheap in-field progesterone immunoassay method, or kit, is available.

Much of the problems in developing such a method and kit are associated with binding anti-progesterone antibody with protein A *Staphylococcus aureus* cells. While it is generally known that such a binding can be effected, the exact procedures remain uncharted.

In addition, following the preparation of a suitable antibody protein A combination, improvement needs to be made in supporting the combination in a proper porous matrix.

The present invention solves many of the problems of the prior art and while it is applicable generally to small molecules, it provides a specific method of binding anti-progesterone antibody with a protein A-positive-formalin-treated, heat-killed *Staphylococcus aureus* cells. Importantly, the present invention provides for a preselected concentration of antibody with a preselected distribution of antibody among the protein A cells.

In addition, the present invention provides for a method of preparing an antibody entrapped porous matrix, as well as providing a method for the production of a kit and a kit for testing the presence of progesterone in animal body fluids, including plasma, milk, saliva and blood. Finally, the apparatus, in accordance with the present invention, provides for self verification of the immunoassay methods of the present invention by indicating a non-specific binding of the enzyme labelled antigen, as will be hereinafter explained in greater detail.

The present invention must be distinguished from immunoassays which are of the "sandwich" type. This last mentioned immunoassay technique involves binding one type of antibody, which is attached to a solid substrate, to an antigen and thereafter adding a solution containing another antibody labelled with an enzyme (or other type of label) and the labelled antibody binds to a different site on the antigen. Hence, the antigen is "sandwiched" between the antibodies.

The sandwich immunoassay methods require an antigen molecule which is large enough to physically accommodate the two antibodies attached to it.

The present invention is primarily directed to the assay of antigens which are too small to bind two antibodies thereto.

SUMMARY OF THE INVENTION

A method of binding antibody with protein A-positive-formalin-treated, heat-killed *Staphylococcus aureus* cells, includes the steps of incubating protein A-positive-formalin-treated, heat-killed *Staphylococcus aureus* cells with antibody to form treated cells of protein A-positive-formalin-treated, heat-killed *Staphylococcus aureus* with antibody attached thereto.

Thereafter, untreated cells of protein A-positive-formalin-treated, heat-killed *Staphylococcus aureus* cells are added to the treated cells.

Subsequently, an agent for cross-linking the antibody with the treated cells is added to the mixture of treated and untreated cells and an agent for deactivating the cross-linking agent is subsequently added to the mixture.

This results in a mixture of treated and untreated cells in which the antibody is concentrated on the treated cells, while at the same time the treated cells are distributed evenly amongst untreated cells which have no antibodies attached thereto. In addition, it is postulated that the cross-linking agent also links the treated and untreated cells with one another.

During the first incubation step of the present invention, conditions are provided which cause a large degree of binding between the protein A and the antibody, which may be anti-progesterone monoclonal antibody.

More specifically, the agent for cross-linking the anti-progesterone monoclonal antibody with the treated cells comprises paraformaldehyde and the agent for deactivating the paraformaldehyde comprises bovine serum albumin.

The hereinabove method is incorporated in the method of the present invention for preparing an antibody entrapped porous matrix.

The hereinabove method of binding of antibody with protein A more specifically includes the steps of incubating protein A-positive-formalin-treated, heat-killed Staphylococcus in a phosphate saline buffer with anti-progesterone antibody to form treated cells having anti-progesterone antibody attached thereto. Thereafter, the treated cells are separated from the phosphate saline buffer and the separated treated cells are washed with additional phosphate saline buffer. The washed treated cells are diluted with protein A-positive-formalin-treated, heat-killed *Staphylococcus aureus* cells in a phosphate saline buffer to form a mixture of treated and untreated cells. To this mixture, paraformaldehyde is added.

Phosphate saline buffer is then added to the paraformaldehyde treated and untreated cells and the treated and untreated cells are separated from the phosphate saline buffer and paraformaldehyde. A following step includes suspending the separated treated and untreated cells in bovine serum albumin and then separating the treated and untreated cells from the bovine serum albumin.

Finally, the separated treated and untreated cells of the hereinabove-referenced step are suspended in the phosphate saline solution and deposited, as hereinafter-discussed in greater detail, in a porous matrix to entrap the untreated and the treated cells having anti-progesterone antibody attached thereto.

A porous matrix may include a porous polyethylene matrix with about 15 micrometer to about 20 micrometer porosity and the treated and untreated cells suspended in a phosphate saline buffer deposited onto only a minor portion of the total surface of the porous matrix.

Therefore, apparatus is provided in accordance with the present invention which is useful in an immunoassay determination of antigen levels in animal body fluid in which color-formation indicates a preselected concentration of a preselected antigen in the animal body fluid.

This apparatus includes a porous matrix having means defining a pore size suitable for entrapping bacteria cells therein. This porous matrix has a first surface and a second surface and a thickness measured therebetween which is substantially smaller than the smallest surface dimension of the porous substrate.

It is also important the the porous matrix, in accordance with the present invention, has a color, or lack of color, suitable for providing a background so that reaction products can be visually distinguished therefrom.

An aliquot of bacterium cells having antibody attached thereto, as hereinabove-described, is disposed within the pores of the porous matrix proximate the porous matrix first surface. The aliquot of antibody, which is capable of combining with a preselected antigen, has a total volume which is substantially smaller than the total volume of the porous matrix. Disposition of the aliquot within the porous matrix is such that the dimensions of the aliquot at the porous matrix first surface is substantially smaller than the smallest surface dimension of the porous matrix.

This is an important feature in that a reaction occurring within the aliquot, caused by reactants provided in the kit of the present invention as hereinafter described, causes color-formation at preselected progesterone levels which occurs in the aliquot only and, as hereinafter described in greater detail, semiquantitatively indicates the level of progesterone.

An absorbant is provided and disposed against the porous matrix second surface for aiding in the withdrawal of fluid therefrom across the entire porous matrix second surface as it passes through the porous matrix.

More specifically, apparatus, in accordance with the present invention, also includes container means which are sealed to an outer perimeter of the porous matrix for supporting fluid poured onto the porous matrix first surface before the fluids pass through the porous matrix and into the absorbant means.

The porous matrix may comprise porous polyethylene, having a pore size of about 15 micrometers to about 20 micrometers, and may be provided in the form of a disk having a diameter of about one inch and a thickness from about 1/16 inch and ⅛ inch.

This apparatus provides an essential portion of the kit of the present invention, with the kit further including a first fluid comprising enzyme labelled antigen of a preselected type for combining with the antibody and a second fluid comprising a first substrate, or a substrate and a chromogen, capable of forming a colored reaction product with the enzyme.

The kit may also provide a second substrate, or a second chromogen, which is capable of forming a reaction product with the enzyme. The second substrate, or a second chromogen, may form a colorless reaction product with the enzyme, or a colored reaction product, and further, the first and second substrates, or a chromogen, may provide oxidation-type reaction products.

The importance of using two substrates, or chromogens, lies in the fact that color-formation can be precisely controlled to indicate a preselected level of progesterone.

It follows that the present invention also includes a method for production of a kit useful for determining the progesterone levels in animal body fluids, with the method including the steps of binding anti-progesterone antibody with protein A and providing for the necessary fluids for conducting the immunoassay.

Similarly, the invention includes a method for testing for the presence of progesterone which includes the steps of preparing a suspension of protein A *Staphylococcus aureus* including the hereinabove-cited steps for the method of binding anti-progesterone antibody with protein A, to provide a treated and untreated cell suspension in phosphate saline buffer, which is deposited upon a porous matrix.

Thereafter, the matrix is contacted with animal body fluid in which the presence of progesterone is to be tested. Following this step, the matrix is contacted with an enzyme labelled progesterone and thereafter rinsed with a phosphate saline buffer. Following the rinsing step, the matrix is contacted with a substrate capable of forming a colored reaction product with the enzyme and thereafter observing the colored reaction product to determine the presence of progesterone.

This method is applicable to body fluids, such as those selected from the group, comprising plasma, milk and saliva.

However, the present invention also provides a method for testing the presence of progesterone in whole blood. This method additionally includes the washing of the porous matrix with a cell-lysing solution after the porous matrix is contacted with whole blood.

BRIEF DESCRIPTION OF THE DRAWINGS

The advantages and features of the present invention will appear in the following description considered in conjunction with the accompanying drawings in which.

DETAILED DESCRIPTION

The present invention incorporates competitive immunoassay method. In this method the antibody is immobilized in the porous matrix and an antigen sample and an enzyme labelled antigen of the same kind compete sequentially for sites on the antibody matrix.

When the excess free enzyme labelled antigen and the free antigen are washed off, a substrate, which is capable of producing a colored reaction product with the enzyme, is added to the matrix and the color develops as a result of the action of the bound enzyme.

If little or no enzyme labelled antigen binds to the antibody, no color develops. This occurs when the majority of the binding sites on the antibody are taken by sample antigen. Hence, the color which develops is inversely proportional to the amount of sample antigen which binds to the antibody, i.e., the more color, the less antigen in the sample, the less color, the more antigen in the sample. This method is well known.

The method of the present invention is useful with many small molecules, however, the present description is limited to anti-progesterone antigens as being typical of such molecules. Specifically, the binding of anti-progesterone antibody with protein A in accordance with the present invention first entails the step of incubating protein A-positive-formalin-treated, heat-killed *Staphylococcus aureus* in a phosphate saline buffer (PBS) with a surfactant, such as Triton X-100 (a nonionic octylphenol ethoxylate type surfactant), with anti-progesterone; mouse monoclonal antibody ($IgG_2$ or $IgG_3$) in PBS. This incubation is maintained for a period of up to approximately three hours at room temperature with continual stirring of the mixture. In this step, the long incubation period is provided so that the antibody saturates essentially all of the sites of the protein A which bind to the antibody.

Following this incubation period, the concentration and amount of antibody is generally too great to allow for accurate analysis at the low levels of progesterone of interest (0 to approximately 20 ng/mL).

Therefore, the amount of antibody is reduced and its concentration is reduced by diluting with untreated protein A cells, untreated cells meaning those not incubated with antibody.

This produces a suspension of antibody treated cells in untreated cells.

Figure 1:
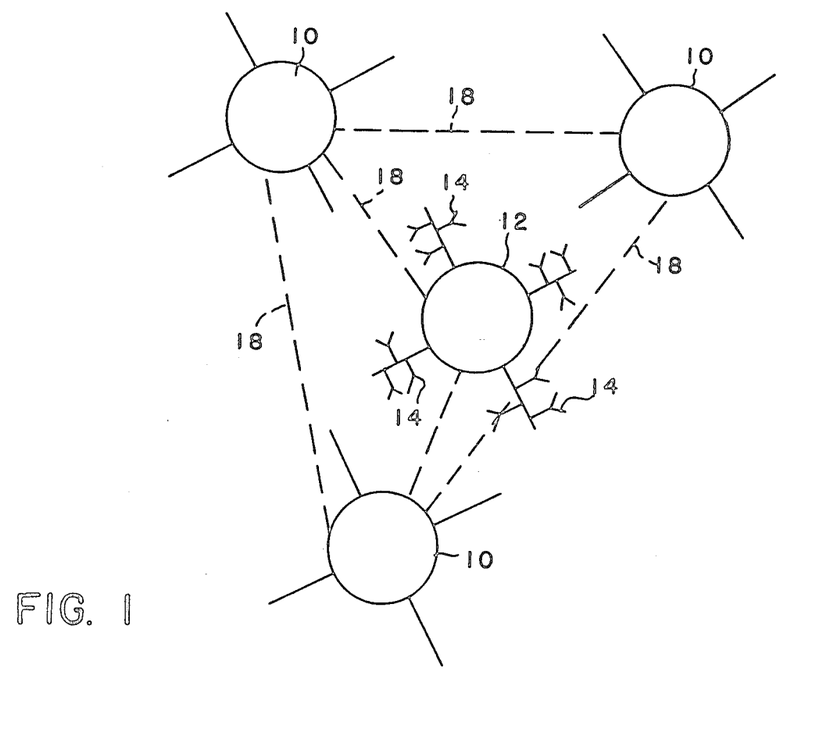
FIG. 1 is a representation of treated and untreated protein A cells showing antibodies attached thereto and illustrating the concentration and distribution of antibody with the protein A cells.

FIG. 1 illustrates the suspension produced in which untreated protein A cells 10 are linked to treated protein A cells 12 which have antibody 14 attached to substantially all of the receptive sites on the protein A.

Figure 2:
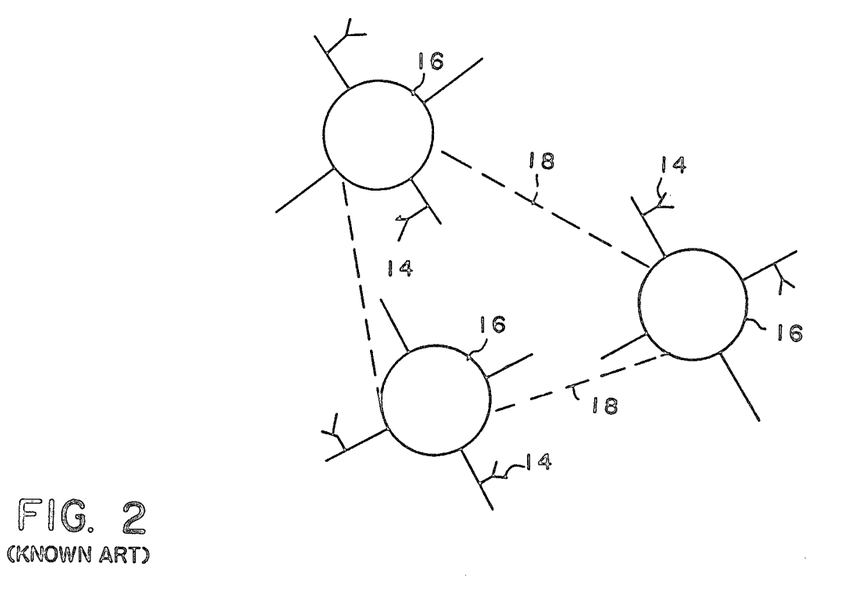
FIG. 2 is a representation of the concentration and distribution of antibody with protein A in accordance with known art.

This is to be contrasted with prior art preparations of protein A antibody suspensions, such as described in U.S. Pat. No. 4,399,229 to Kelton, in which the sites on the protein A are not saturated, but rather each of the protein cells has non-saturated binding with antibody to produce the concentration of antibody necessary for the analysis. (See FIG. 2 in which 16 represents protein A cells having unsaturated sites). Such concentrations as represented in FIG. 2 are produced by allowing the protein A and the antibody to incubate for the shorter periods of time with diluted antibody.

In the present invention, the antibody saturated protein A cells are diluted with untreated cells to achieve the proper concentration of antibody. In addition, the dilution with untreated cells, rather than some other aqueous solution, contributes to the stability of the suspension. It has been found that the antibody protein A suspension remains stable for several days at room temperature. Room temperature stability is important when the suspension is to be used in an in-field test device. It is also important in eliminating refrigerated shipping costs, and the like.

After the mixture of treated and untreated cells are washed with PBS, they are diluted to a 2 percent antibody-treated cell suspension in PBS and thereafter paraformaldehyde is added, in order to cross-link the antibody molecules 14 to the protein A cells 12 so that they cannot be displaced by any miscellaneous antibody molecules present in a serum sample. In addition, it is postulated that this step also chemically cross-links the cells to one another as represented by the dotted lines 18 in FIGS. 1 and 2.

Following cross-linking, the cells are washed with PBS, thereafter centrifuged and then resuspended in a bovine serum albumin (BSA) for 15 to 30 minutes at room temperature in order to bind all of the remaining paraformaldehyde sites to prevent non-specific adsorption thereon of the sample, or enzyme labelled antigen.

In competitive enzyme immunoassay, such as the present invention, the effect of antibody amount and concentration on assay sensitivity is very great at the levels of progesterone antigen of interest, namely, 0 to about 20 ng/ml.

As hereinbefore discussed, it is very important to have an extremely sensitive and accurate assay method in order to correctly detect the difference between progesterone levels in the 0–5 ng/ml and progesterone levels above 10 ng/ml.

Figure 4:
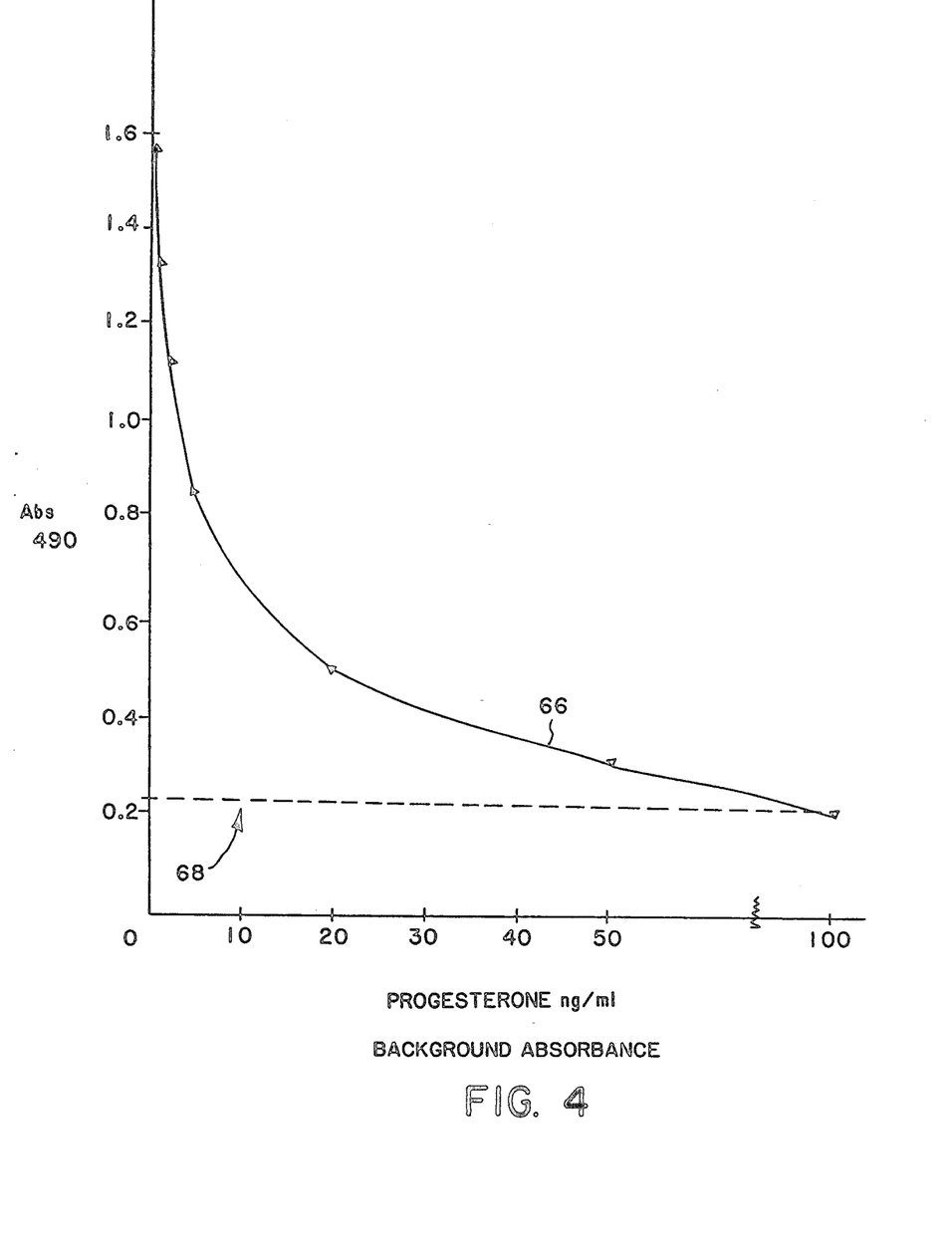
FIG. 4 is a plot of absorbance vs. progesterone for a typical quantitative EIA assay for milk illustrating a residual background color caused by enzyme-label remaining bound to antibody.

FIG. 4 shows three plots 60, 62, 64 of the change in absorbance (Abs=I/Io) measured quantitatively with a spectrophotometer at $\uparrow$ =490 nm, vs. progesterone level in serum samples. These progesterone enzyme immunoassay data (EIA) were obtained using a quantitative microtiter plate format (not the method of the present invention) in order to demonstrate the sensitivity of color-formation when the antibody concentration is varied by approximately a factor of five (MAb=[x] to MAb=[x/5]. The enzyme-label concentration was held constant at 100 ng/ml and the substrate used was o-phenylenediamine with $H_2O_2$.

Since the human eye is most sensitive in the absorbance range of 0–1, it can be seen that the change in color in the progesterone level of 0–20 ng/ml is dramatic.

Figure 3:
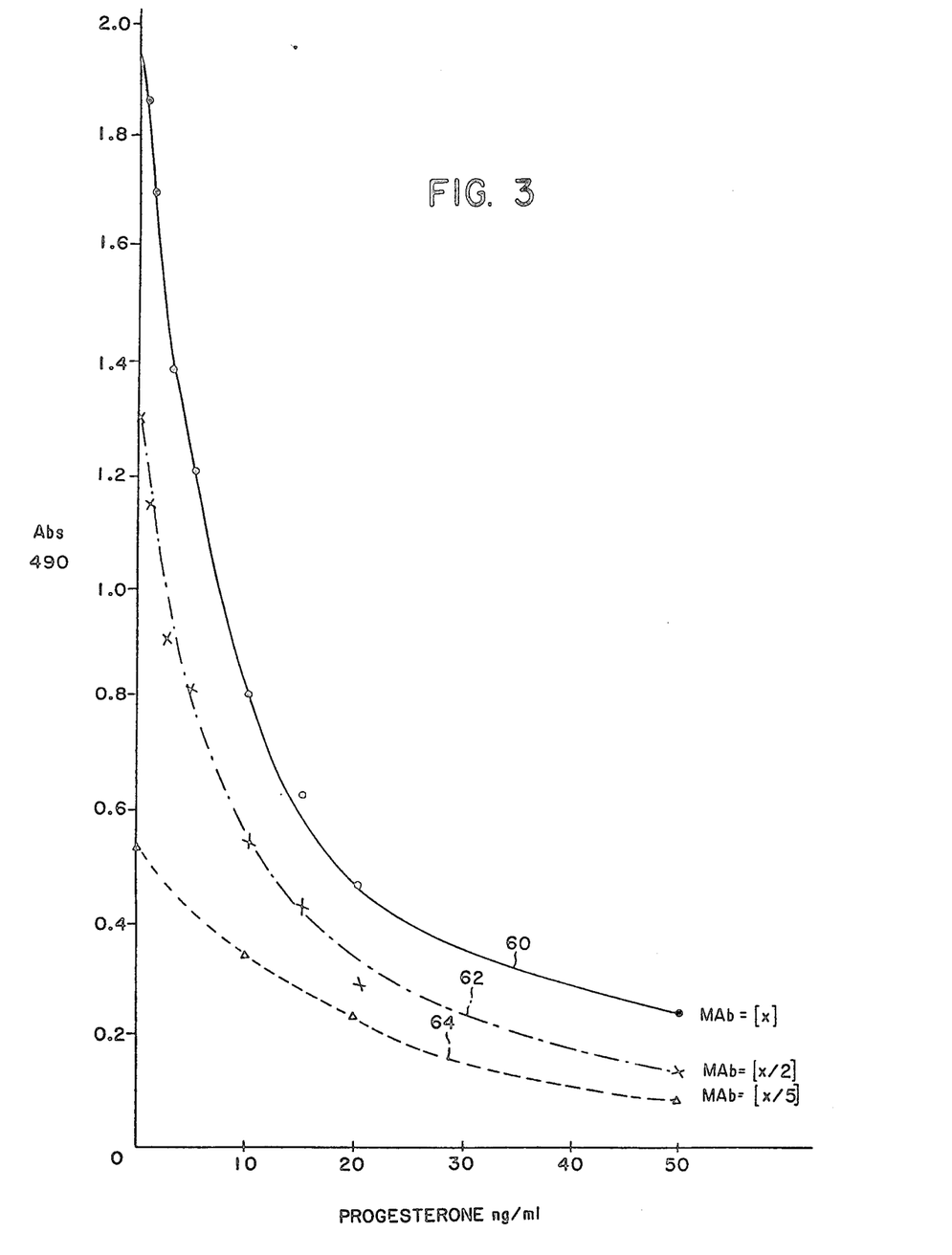
FIG. 3 is a plot of absorbance vs. progesterone level showing the effect of antibody concentration on assay sensitivity.

FIG. 3 shows a plot 66 of the change in absorbance (Abs=I/Io) measured quantitatively with a spectrophotometer at $\uparrow$ =490 nm, vs. progesterone level in milk samples. Also shown is absorbance attributed to background occurring when o-phenylenediamine is used as a substrate. This background color 68 arises because in the competitive immunoassay method some enzyme labelled antigen remains attached to the antibody despite the concentration of antigen in the sample. For example, if the sample has very high concentrations of progesterone, such as 100 ng/ml, it does not completely saturate all the antibody sites and have some enzyme-labelled antigen remains bound to the antibody resulting in a residual background color as shown in FIG. 4.

Figure 5:
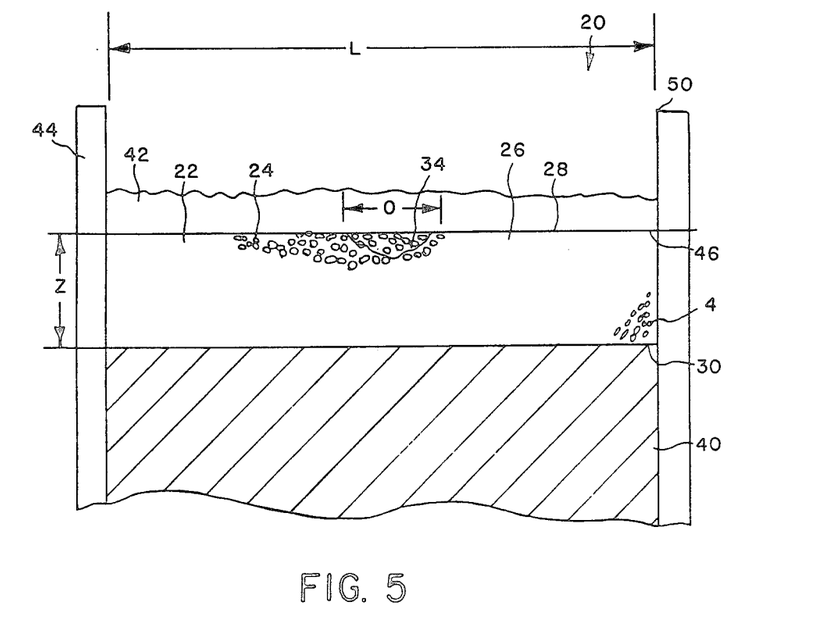
FIG. 5 is a cross-section view of apparatus in accordance with the present invention.

Diagrammatically shown in FIG. 5, is apparatus 20 useful in immunoassay determination of antigen levels in animal body fluid, in accordance with the present invention.

Generally, a porous matrix 22 is provided which has a pore 24 size suitable for entrapping bacterium cells therein. Suitable pore size has been found to be about 15 microns to about 20 microns.

The porous matrix may have the shape of a disk 26 (see FIG. 5) with a first surface 28 and a second surface 30 with a thickness, t, measured therebetween of about 1/16 of an inch to about ⅛ inch, the disk having a diameter of approximately one inch.

Preferably, the porous matrix is comprised of polyethylene, having a white color, which is suitable for providing background so that reaction products can be visually distinguished therefrom. In addition, the porous polyethylene is treated, in a manner well known in the art, to be hydrophilic.

Within the porous matrix, proximate the first surface 28, an aliquot 34 of bacterium cells having antibody attached thereto, is entrapped in the pores 24.

The volume of the aliquot 34 is preselected and fixes the amount of antibody available for the assay. As hereinbefore-discussed, the effect of antibody amount and concentration is very important on assay sensitivity.

Since in the present invention the amount and concentration of antibody in the aliquot is preselected and fixed, the amounts of sample, labelled antigen and substrates are not critical. Hence, the methods of the present invention are highly suited to in-field testing where the addition of the sample, labelled antigen and substrate may not be accurate.

As hereinbefore-discussed in connection with a method of binding anti-progesterone antibody with protein A, the antibody is capable of combining with a preselected antigen, such as progesterone.

The aliquot 34 has a total volume which is substantially smaller than total volume of the porous matrix 22 and the aliquot has a dimension, d, at the porous matrix first surface 28, which is substantially smaller than the diameter D of the porous matrix disk 26.

As shown in FIG. 5, an absorbant pad 40, or the like, is disposed against the porous matrix second surface 30 for withdrawing fluid (not shown) therefrom across the entire porous matrix second surface 30.

In order to support fluid 42 poured onto the porous matrix first surface 28, a cylinder 44 may be sealed to the outer perimeter 46 of the porous matrix disk 26.

As hereinbefore indicated, the bacterium cells may be protein A-positive-formalin-treated, heat-killed *Staphylococcus aureus* cells and the antibody may be anti-progesterone monoclonal antibody.

The apparatus 20 may be used in the field to assay for progesterone level in plasma or milk sample, as follows:

Eight to ten drops of plasma, or fresh milk samples, are added dropwise to the center of the porous matrix disk 26. After a wait of 5 to 6 minutes, 5 to 6 drops (80–400 ng/ml) of enzyme labelled progesterone, which may be horseradish peroxidase-labelled progesterone is added and allowed to pass through the porous matrix 22 into the absorbant 40 with approximately 30 seconds to 2 minutes provided for this to occur.

Thereafter, the porous matrix is rinsed with approximately 2 to 3 milliliters of distilled water and 5 to 20 drops of substrate is added which approximately fills the container 44 to the top 50 thereof.

The substrate may be tetramethyl benzidine in $10^{-3}$M $H_2O_2$, pH 5. After about 5 minutes, the appearance of a colored spot (see FIG. 6A) which is blue for tetramethyl benzidene, is indicative of low progesterone. The absence of a colored spot (FIG. 6C) corresponds to higher progesterone level.

The assay can be used to analyze for progesterone levels in the 1–50 ng/ml, which is commonly found in milk and serum samples. The assay can also be used to analyze for progesterone levels in the 1–10 ng/ml region, this critical region being for the detection of estrus and early pregnancy. The levels tested for are adjusted by the concentration of the fluids added.

As hereinbefore noted, a background color may develop in the aliquot because even at high progesterone levels some enzyme labelled antigen remains bound to the antibody.

The background color cannot be eliminated by varying the enzyme concentration or the period of contact time between the antibody and antigen.

However, it has been found that in accordance with the present invention, the use of two or more substrates, or chromogens, can eliminate the background color and achieve an accurate cutoff point, such that above a certain progesterone level no colored spot is seen.

In this embodiment two chromogens are used in combination with the enzyme HRP, so that one chromogen forms a colorless (invisible oxidation product) while the second chromogen forms a visible oxidation product.

Suitable colorless and colored reaction products other than oxidation products may also be utilized.

Figure 6:
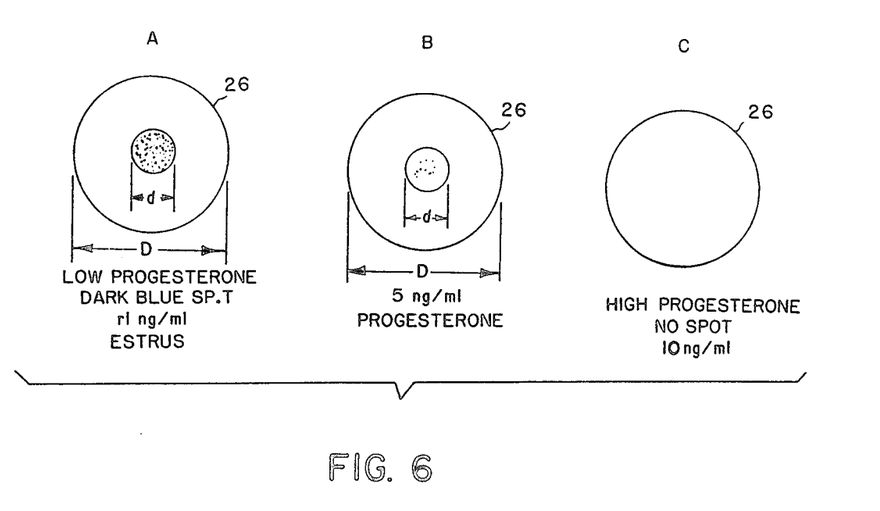
FIG. 6 is a representation of the use and results of the present invention in determining the level of progesterone in animal body fluids.

FIG. 6 shows the results of an enzymeimmunoassay test performed in accordance with the present invention using three samples, one having low progesterone (~1 ng/ml) a second having 5 ng/ml progesterone and a third having high progesterone (10 ng/ml).

Two substrates, namely, tetramethyl benzidene (TMB) (2 mmol/l) and nicotinamide adenine dinucleotide (NADH) (0.4 mmol/l) with hydrogen peroxide (2 mmol/l) was added to develop the test color and these results illustrated in FIG. 6.

No background color occurs at the high progesterone level (FIG. 6C) because of the colorless oxidation product formed between NADH and the enzyme. The oxidized radical form of TMB with enzyme has a blue color of approximately 652 nm wavelength, but the intensity of this color is adjusted by use of the second chromogen.

It may be possible to utilize the bound antiprogesterone antibody with protein A in other configurations, such as on to a flat dipstick which may be dipped into serum, or other body fluids, or in a test tube configuration in which the sides of which would be coated with the bacterium antibody combination.

If a dipstick (not shown) were utilized, it would be dipped into a sample for a 5 minute incubation, then washed off and dipped into an enzyme solution, washed and finally dipped into a substrate solution to develop color.

However, the preferred apparatus of the present invention hereinbefore discussed is important because it provides means for determining the occurrence of non-specific binding of enzyme labelled antigen within the porous substrate. This determination is manifest by color-formation in the porous substrate in areas other than within the aliquot. If the porous matrix is not rinsed properly, non-specific binding of the enzyme labelled antigen may occur outside the aliquot 34.

When this happens, the color appearance is not a specific dot, having a diameter of the aliquot, as shown in FIGS. 6A and 6B, but rather is a blurry pattern which extends from the aliquot across the surface 28 of the porous matrix disk 26 and/or discolors the entire porous matrix for surface 28.

Thus, the present invention includes means for verifying that the proper steps are taken in rinsing and adding of the various fluids set forth for performing an assay for an antigen, such as progesterone.

The following are specific examples and preferred embodiments of the present invention. There is no intention of the claims to be limited thereto, since many variations are within the skill of the art.

For instance, while the examples specifically recite enzymes, such as horseradish peroxidase (HRP), others which may be used are alkaline phosphatase, galactosidase, glucose oxidase, or catalase.

Two preferred enzymes include HRP and alkaline phosphatase. In combination with HRP, preferred substrates which result in highly visible colors are tetramethyl benzidine/peroxide, resulting in a blue color, or 2,2'-azinodi(3-ethylbenzothiazoline-6-sulphonate) (ABTS)/peroxide, resulting in a green color. Preferred substrates in combination with alkaline phosphatase include phenolphthalein phosphate (red or pink), indoxyl phosphate (blue), 5-bromo-4-chloro-3-indoxyl phosphate (blue), or thymolphthalein phosphate (blue).

EXAMPLE 1

Preparation of antibody-entrapped filter matrix (Disk coating procedure)

Four parts 10% protein A-formalin-treated, heat-killed *Staphylococcus aureus* (in physiological phosphate saline buffer (PBS), pH 7.2, with 0.1% Triton X-100) are incubated with one part anti-progesterone monoclonal antibody ($IgG_2$ or $IgG_3$) (in the same buffer) (such that the final concentration of antibody is 3–4 mg antibody/ml) for 3 hours at room temperature with stirring.

Cells are washed 2X with two volumes of the same phosphate buffer with Triton X-100 and diluted to a 2% antibody-treated cell suspension with the same buffer.

The 2% antibody-treated cells are diluted to 1/20, 1/50, 1/75 with 1% untreated cells. An equivalent volume of 1% paraformaldehyde is added to this combined cell suspension. This cell suspension is agitated with paraformaldehyde at 37° C. for 45 minutes. (This step cross-links antibody molecules to the protein A cells so that they cannot be displaced by any miscellaneous antibody molecules present in a serum sample. This step also cross-links the cells to one another).

Several volumes of PBS with Triton X-100 are added and the cells are centrifuged, washed, and then resuspended in 1% bovine serum albumin (BSA) (in PBS) for 15-30 minutes at room temperature. (The purpose of the BSA is to bind up all the remaining paraformaldehyde sites in order to prevent non-specific adsorption of the sample or enzyme).

An aliquot of 20 μl of 1% cell suspension is added to the center of white porous polyethylene disk (15-20 mμ porosity). The disk is approximately 1 inch in diameter and ⅛ inch or 1/16 inch in thickness.

Excess moisture is removed by putting the disks in a vacuum dessicator for one hour.

EXAMPLE II

Assay for Progesterone in a plasma or milk sample

All steps are carried out at about room temperature (22°-25° C.). (At other temperatures, the relative times need to be adjusted).

1. Add 8-10 drops of plasma or fresh milk sample (dropwise) to the center of the disk. Wait for 5-6 minutes.
2. Add 5-6 drops of enzyme-labelled progesterone (e.g. 80-400 ng/ml of horseradish-peroxidase-labelled progesterone). Wait for 30 seconds-2 minutes.
3. Rinse with approximately 2-3 ml distilled water.
4. Add substrate 5-20 drops (e.g. tetramethyl benzidine in $10^{-3}M$ $H_2O_2$, pH 5). Wait for 5 minutes.

The appearance of a colored spot (e.g. blue for tetramethyl benzidine) is indicative of low progesterone. The absence of a colored spot corresponds to a higher progesterone level. The assay can be used to analyze for progesterone levels in the 1-50 ng/ml level, commonly found in milk and serum samples. The assay can also be used to analyze for progesterone levels in the 1-10 ng/ml region, the critical region for the detection of estrus and early pregnancy.

EXAMPLE III

Assay for progesterone in a whole blood sample

A fresh blood sample which has been collected in a tube containing an anticoagulent such as heparin or EDTA should be used. All steps are carried out at room temperature (22°-25° C.).

1. Add 5-6 drops of whole blood to the center of the disk. Wait for 5-6 minutes.
2. Wash the disk thoroughly with 2-4 ml of a cell-lysing solution such as distilled water, a solution of sodium dodecyl sulfate (SDS) (or a variety of other reagents), so that all the red blood color disappears.
3. Add 5-6 drops of enzyme-labelled progesterone (e.g. 80-400 ng/ml of horseradish-peroxidase-labelled progesterone). Wait for 30 seconds-2 minutes.
3. Rinse with approximately 2-3 ml distilled water.
4. Add substrate, 5-20 drops, by simply filling the upper reservoir of the holder. The substrate is (for example, tetramethyl benzidine in $10^{-3}M$ $H_2O_2$, pH 5). Wait for 5 minutes.

The appearance of a colored spot (e.g. blue when tetramethyl benzidine is the substrate and HRP is the enzyme) is indicative of low progesterone. The absence of a colored spot corresponds to a higher progesterone level. The assay can be used to analyze for progesterone levels in the 1-50 ng/ml level, commonly found in blood samples. The assay can also be used to analyze for progesterone levels in the 1-10 ng/ml region.

By adjusting the amount of antibody incorporated in the disk and the amount and concentration of enzyme-label used, the assay can be adjusted so that it is sensitive at the desired level.

What is claimed is:

1. A method of binding and stabilizing antibody with protein A-positive-formalin-treated, heat-killed *Staphylococcus aureus* cells comprising the steps of:
   a) incubating protein A-positive-formalin-treated, heat-killed *Staphylococcus aureus* cells with antibody to form treated cells of protein A-positive-formalin-treated, heat-killed *Staphylococcus aureus* with antibody attached thereto;
   b) adding untreated cells of protein A-positive-formalin-treated, heat-killed *Staphylococcus aureus* to the treated cells;
   c) adding to the treated and untreated cells an agent for cross-linking the antibody with the treated cells;
   d) adding to the treated and untreated cells an agent for deactivating the agent for cross-linking the antibody with the treated cells.

2. A method of binding and stabilizing anti-progesterone antibody with protein A-positive-formalin-treated, heat-killed *Staphylococcus aureus* cells comprising the steps of:
   a) incubating protein A-positive-formalin-treated, heat-killed *Staphylococcus aureus* cells with anti-progesterone antibody to form treated cells of protein A-positive-formalin-treated, heat-killed *Staphylococcus aureus* with anti-progesterone antibody attached thereto;
   b) adding untreated cells of protein A-positive-formalin-treated, heat-killed *Staphylococcus aureus* to the treated cells;
   c) adding to the treated and untreated cells an agent for cross-linking the anti-progesterone antibody with the treated cells;
   d) adding to the treated and untreated cells an agent for deactivating the agent for cross-linking the anti-progesterone antibody with the treated cells.

3. The method according to claim 2 wherein the agent for cross-linking the anti-progesterone antibody with the treated cells comprises paraformaldehyde.

4. The method according to claim 3 wherein the agent for deactivating the agent for cross-linking the anti-progesterone monoclonal antibody to the treated cells comprises bovine serum albumin.

5. The method of claim 4 wherein the anti-progesterone antibody comprises anti-progesterone monoclonal antibody.

6. The method according to claim 5 wherein the incubation is conducted for a period of time to saturate substantially all of the sites on the protein A receptive to antibody with antibody.

7. The method according to claim 6 wherein the incubation is conducted at room temperature for a period up to about three hours.

8. A method for preparing an antibody-entrapped porous matrix comprising the steps of:
   a) incubating protein A-positive-formalin-treated, heat-killed *Staphylococcus aureus* cells in a phosphate saline buffer with anti-progesterone antibody to form treated cells having anti-progesterone antibody attached thereto;
   b) separating the treated cells from the phosphate saline buffer;
   c) washing the separated treated cells with phosphate saline buffer;
   d) diluting the washed treated cells with protein A-positive-formalin-treated, heat-killed *Staphylococcus aureus* cells in a phosphate saline buffer to form a mixture of treated and untreated cells;

e) adding paraformaldehyde to the treated and untreated cells;

f) adding phosphate saline buffer to the paraformaldehyde, treated and untreated cells;

g) separating the treated and untreated cells from the phosphate saline buffer and paraformaldehyde;

h) suspending the separated treated and untreated cells in bovine serum albumin;

i) separating the treated and untreated cells from the bovine serum albumin;

j) suspending the separated treated and untreated cells of step i) in a phosphate saline buffer; and k) depositing a precise preselected amount of the treated and untreated cells suspended in phosphate saline buffer onto a porous matrix to entrap the untreated cells and the treated cells having anti-progesterone antibody attached thereto.

9. The method according to claim 8 wherein the treated and untreated cells suspended in phosphate saline buffer are deposited onto a minor portion of the total surface of the porous matrix and said porous matrix has a pore size greater than the size of treated and untreated cells.

10. The method according to claim 9 wherein the porous matrix comprises porous polyethylene with about 15 μm to about 20 μm porosity.

11. The method according to claim 10 wherein the porous matrix comprises a disk having a diameter of about on inch and a thickness between about 1/16 inch and about ⅛ inch, and an aliquot of about 20 μl of the treated and untreated cells is deposited onto one side of said disk.

12. The method according to claim 11 further comprising the step of dessicating the disk after the treated and untreated cells in phosphate saline buffer have been deposited thereon.

13. The method according to claim 8 wherein the phosphate saline buffer comprises a surfactant to reduce non-specific binding between said anti-progesterone antibody and said protein A-positive-formalin-treated, heat-killed *Staphylococcus aureus* cells.

14. The method according to claim 13 wherein the surfactant comprises polyethylene glycol p-isooctylphenyl ether.

15. A kit for enzyme immunoassay determination of antigen levels in animal body fluid using a competitive immunoassay method in which color-formation indicates the concentration of a preselected antigen in the animal fluid, said kit comprising:

a porous matrix having means defining a pore size suitable for entrapping bacterium cells therein, said porous matrix having color means for providing a background in order that reaction products can be visually distinguished from the porous matrix;

an aliquot of bacterium cells having an antibody attached thereto disposed within the pores of the porous matrix, said antibody being capable of combining with a preselected antigen;

a first fluid comprising enzyme-labelled antigen of the preselected type for combining with said antibody; and a second fluid comprising a first substrate capable of forming a colored reaction product with the enzyme and a second substrate capable of forming a reaction product with the enzyme.

16. The kit according to claim 15 further comprising container means sealed to the outer perimeter of said porous substrate for supporting fluid poured onto said porous matrix first surface before said fluid passes through the porous matrix.

17. The kit according to claim 16 wherein the bacterium cells comprise protein A-positive-formalin-treated, heat-killed *Staphylococcus aureus* cells and the antibody comprises anti-progesterone monoclonal antibody.

18. The kit according to claim 15 wherein the second substrate forms a colorless reaction product with the enzyme.

19. The kit according to claim 18 wherein the first substrate forms a first colored product with said enzyme, said second substrate forms a second colored product with said enzyme, and said first and second colored products have a color different from each other.

20. The kit according to claim 19 wherein the porous matrix comprises white porous polyethylene having a pore size of about 15 μm to about 20 μm.

21. The kit according to claim 20 wherein the porous matrix comprises a disk having a diameter of about one inch and a thickness between about 1/16 inch and about ⅛ inch.

22. The kit according to claim 21 wherein the volume of the aliquot is about 20 μl.

23. The kit according to claim 15 wherein the porous matrix and the aliquot of bacterium cells therein provide means for determining the occurrence of non-specific binding of enzyme-labelled antigen within the porous matrix, said determination being manifest by color-formation in said porous matrix in areas other than within said aliquot.

24. A method for the production of a kit useful for determining progesterone levels in animal body fluids, said method comprising the steps of:

a) incubating protein A-positive-formalin-treated, heat-killed *Staphylococcus aureus* cells in a phosphate saline buffer with anti-progesterone antibody to form treated cells having anti-progesterone antibody attached thereto;

b) separating the treated cells from the phosphate saline buffer;

c) washing the separated treated cells with phosphate saline buffer;

d) diluting the washed treated cells with protein A-positive-formalin-treated, heat-killed *Staphylococcus aureus* cells in a phosphate saline buffer to form a mixture of treated and untreated cells;

e) adding paraformaldehyde to the treated and untreated cells;

f) adding phosphate saline buffer to the paraformaldehyde, treated and untreated cells;

g) separating the treated and untreated cells from the phosphate saline buffer and paraformaldehyde;

h) suspending the separated treated and untreated cells in bovine serum albumin;

i) separating the treated and untreated cells from the bovine serum albumin;

j) suspending the separated treated and untreated cells of step i) in a phosphate saline buffer;

k) depositing the treated and untreated cells suspended in phosphate saline buffer on a porous matrix to entrap the untreated cells and the treated cells having anti-progesterone antibody attached thereto;

l) disposing said porous matrix in a container suitable for exposing the porous matrix to fluids for reacting with the treated cells entrapped thereon;

m) providing a first fluid comprising enzyme-labelled progesterone for contacting with said porous matrix; and n) providing a second fluid comprising a first substrate capable of forming a colored reaction product when contacted with the enzyme.

25. The method according to claim 24 wherein the first substrate forms a colored reaction product when contacted with the enzyme.

26. The method according to claim 25 wherein the second fluid further comprises a second substrate capable of forming a reaction product when contacted with the enzyme.

27. The method according to claim 26 wherein the second substrate forms a colorless reaction product when contacted with the enzyme.

28. The method according to claim 26 wherein the first substrate forms a first colored oxidation product when contacted with the enzyme, said second substrate forms a second colored oxidation product when contacted with the enzyme, and said first and second colored oxidation products having a color different from each other.

29. A method for testing for the level of progesterone in an animal body fluid comprising the steps of:

A) preparing a suspension of protein A *Staphylococcus aureus* comprising the steps of:
   a) incubating protein A-positive-formalin-treated, heat-killed *Staphylococcus aureus* cells in a phosphate saline buffer with anti-progesterone antibody to form treated cells having anti-progesterone antibody attached thereto;
   b) separating the treated cells from the phosphate saline buffer;
   c) washing the treated cells with phosphate saline buffer;
   d) diluting the washed treated cells with protein A-positive-formalin-treated, heat-killed *Staphylococcus aureus* cells in a phosphate saline buffer to form a mixture of treated and untreated cells;
   e) adding paraformaldehyde to the treated and untreated cells;
   f) adding phosphate saline buffer to the paraformaldehyde, treated and untreated cells;
   g) separating the treated and untreated cells from the phosphate saline buffer and formaldehyde;
   h) suspending the separated treated and untreated cells in bovine serum albumin;
   i) separating the treated and untreated cells from the bovine serum albumin;
   j) suspending the separated treated and untreated cells of step h) in a phosphate saline buffer;

B) depositing an aliquot of the treated and untreated cells suspended in phosphate saline buffer onto a porous matrix to entrap the untreated and treated cells;

C) contacting the matrix with an animal body fluid in which the presence of progesterone is to be tested;

D) after Step C contacting the matrix with enzyme-labelled progesterone;

E) after Step D rinsing the matrix with a phosphate saline buffer;

F) thereafter contacting the matrix with a substrate capable of forming a colored reaction product when contacted with the enzyme; and G) observing the colored reaction product to determine the presence of progesterone.

30. The method according to claim 29 wherein the animal body fluid is selected from a group consisting of plasma, milk and saliva.

31. The method according to claim 29 wherein the aliquot of treated and untreated cells deposited onto the porous matrix is disposed in the pores of the porous matrix proximate the surface of the porous matrix, said aliquot having a total volume which is substantially smaller than the total volume of the porous matrix and having dimensions at the porous matrix surface which are substantially smaller than the smallest surface dimension of the porous matrix, and the method further comprising the step of determining the occurrence of non-specific binding of the enzyme-labelled progesterone within the porous matrix by observing color-formation in said porous matrix in areas other than with said aliquot.

32. A method for testing for the level of progesterone in whole blood comprising the steps of:

A) preparing a suspension of protein A *Staphylococcus aureus* comprising the steps of:
   a) incubating protein A-positive-formalin-treated, heat-killed *Staphylococcus aureus* cells in a phosphate saline buffer with anti-progesterone antibody to form treated cells having anti-progesterone antibody attached thereto;
   b) separating the treated cells from the phosphate saline buffer;
   c) washing the treated cells with phosphate saline buffer;
   d) diluting the washed treated cells with protein A-positive-formalin-treated, heat-killed *Staphylococcus aureus* cells in a phosphate saline buffer to form a mixture of treated and untreated cells;
   e) adding paraformaldehyde to the treated and untreated cells;
   f) adding phosphate saline buffer to the paraformaldehyde, treated and untreated cells;
   g) separating the treated and untreated cells from the phosphate saline buffer and paraformaldehyde; and
   h) suspending the separated treated and untreated cells in bovine serum albumin;
   i) separating the treated and untreated cells from the bovine serum albumin;
   j) suspending the separated treated and untreated cells of step i) in a phosphate saline buffer;

B) depositing an aliquot of the treated and untreated cells suspended in phosphate saline buffer onto a porous or matrix to entrap the untreated and treated cells;

C) contacting the porous matrix with a whole blood in which the level of progesterone is to be tested;

D) washing the porous matrix with a cell-lysing solution;

E) after Step D, contacting the porous matrix with enzyme-labelled progesterone;

F) after Step E, rinsing the porous matrix with a phosphate buffer;

G) thereafter contacting the porous matrix with a substrate capable of forming a colored product when contacted with the enzyme; and H) observing the colored product to determine both the presence of progesterone and non-specific binding of the enzyme labelled progesterone.

33. The method according to claim 32 wherein the aliquot of treated and untreated cells deposited onto the porous matrix is disposed in the pores of the porous matrix proximate the surface of the porous matrix, said aliquot having a preselected total volume which substantially smaller than the total volume of the porous matrix and having dimensions at the porous matrix surface which are substantially smaller than the smallest surface dimension of the porous matrix, and the method further comprising the step of determining the occurrence of non-specific binding of the enzyme-labelled progesterone within the porous matrix by observing color-formation in said porous matrix in areas other than with said aliquot.

34. A method for enzyme immunoassay determination of antigen levels in animal body fluid comprising:
contacting animal body fluid comprising a preselected antigen with a carrier having an antibody attached thereto capable of binding with said preselected antigen;
contacting the animal body fluid with the preselected antigen having an enzyme attached thereto;
contacting the animal body fluid with a first substrate capable of forming a visible colored reaction product when contacted with the enzyme;
controlling the color intensity of the visible colored reaction product by the addition of a second substrate capable of reacting with said enzyme and observing the colored reaction product to determine the presence of antigen.

35. A method for enzyme immunoassay determination of antigen levels in animal body fluid comprising:
providing protein A-positive-formalin-treated, heat-killed *Staphylococcus aureus* cells with antibody attached thereto, said antibody being capable of binding to a preselected antigen;
contacting the antibody attached protein cells with an animal body fluid comprising the preselected antigen;
contacting the antibody attached protein cells with the preselected antigen having an enzyme attached thereto;
contacting the antibody attached protein cells with a first substrate capable of forming a visible colored reaction product when contacted with the enzyme;
contacting the antibody attached protein cells with a second substrate capable of controlling the intensity of the visible color of the visible colored reaction product produced by contact of the first substrate with the enzyme and observing the colored reaction product to determine the presence of antigen.

36. The method according to claim 35 wherein the step of providing antibody attached protein includes depositing the antibody attached protein into a porous matrix having color means for providing a background so that reaction product can be visually distinguished from the porous matrix.

37. The method according to claim 36 wherein the first and second substrates are simultaneously contacted with the antibody attached protein cells.

38. The method according to claim 37 wherein the second substrate is capable of forming a colorless reaction product when contacted with the enzyme.

39. The method according to claim 37 wherein the second substrate is capable of forming a colored reaction product when contacted with the enzyme, said last mentioned colored reaction product having a different color than the reaction product formed by contact of the first substrate with the enzyme.

40. The method according to claim 37 wherein the antigen is progesterone, the first substrate is tetramethyl benzidine and the second substrate is nicotinamide adenine dinucleotide.

* * * * *